US008210179B2

(12) United States Patent
Eaton et al.

(10) Patent No.: US 8,210,179 B2
(45) Date of Patent: Jul. 3, 2012

(54) PATIENT INTERFACE WITH FOREHEAD SUPPORT SYSTEM

(75) Inventors: Jason P. Eaton, Hunker, PA (US); Richard J. Lordo, Butler, PA (US); Lance Busch, Trafford, PA (US); Peter Chi Fai Ho, Pittsburgh, PA (US)

(73) Assignee: RIC Investments, LLC, Wilmington, DE (US)

( * ) Notice: Subject to any disclaimer, the term of this patent is extended or adjusted under 35 U.S.C. 154(b) by 928 days.

(21) Appl. No.: 11/480,592

(22) Filed: Jul. 3, 2006

(65) Prior Publication Data
US 2006/0249157 A1 Nov. 9, 2006

Related U.S. Application Data

(63) Continuation of application No. 10/654,379, filed on Sep. 3, 2003, now Pat. No. 7,069,932.

(60) Provisional application No. 60/408,836, filed on Sep. 6, 2002.

(51) Int. Cl.
*A62B 18/08* (2006.01)
*A62B 18/02* (2006.01)

(52) U.S. Cl. ......... 128/206.24; 128/207.11; 128/206.21; 128/206.28; 128/205.25; 403/82

(58) Field of Classification Search ............. 128/201.23, 128/201.24, 206.21, 206.24, 206.27, 206.28, 128/207.11, 207.13, 207.17, 205.25, 206.23; 403/63, 82, 83, 103
See application file for complete search history.

(56) References Cited

U.S. PATENT DOCUMENTS

| 4,907,584 | A | 3/1990 | McGinnis |
| 5,042,478 | A | 8/1991 | Kopala et al. |
| 5,243,971 | A | 9/1993 | Sullivan et al. |
| 5,517,986 | A | 5/1996 | Starr et al. |
| 5,570,689 | A | 11/1996 | Starr et al. |
| 6,119,693 | A | 9/2000 | Kwok et al. |
| D439,326 | S | 3/2001 | Hecker et al. |
| 6,357,441 | B1 | 3/2002 | Kwok et al. |

(Continued)

FOREIGN PATENT DOCUMENTS
EP 0958841 11/1999
(Continued)

OTHER PUBLICATIONS

Map Medizin-Technologie GmbH, Papillion ©, 2002, Germany.

*Primary Examiner* — Justine Yu
*Assistant Examiner* — Valerie L Skorupa
(74) *Attorney, Agent, or Firm* — Michael W. Haas

(57) ABSTRACT

A patient interface having a forehead support adjustably. The forehead support assembly includes a support arm that is adjustably mounted to the mask shell, thereby allowing the adjustment of the distance between the forehead support bracket and the mask shell in order to adjust for patient's of different sizes. A forehead support bracket is pivotally connected to the support arm. The pivoting forehead support bracket is self-aligning to allow the forehead pad to remain parallel to the patient's forehead at all times, thus enhancing comfort and stability. The forehead support bracket is removable from the support arm, allowing the headgear (with support bracket attached) to be donned separately from the mask and support arm. The forehead support bracket in one embodiment has a forehead pad formed from the headgear itself.

17 Claims, 10 Drawing Sheets

U.S. PATENT DOCUMENTS

| | | |
|---|---|---|
| 6,374,826 B1 | 4/2002 | Gunaratnam et al. |
| 6,520,182 B1 * | 2/2003 | Gunaratnam .............. 128/206.27 |
| 6,532,961 B1 * | 3/2003 | Kwok et al. ............. 128/206.21 |
| 6,615,834 B2 | 9/2003 | Gradon et al. |
| 6,691,708 B2 | 2/2004 | Kwok et al. |
| 6,796,308 B2 | 9/2004 | Gunaratnam et al. |
| 6,823,869 B2 * | 11/2004 | Raje et al. ................ 128/206.24 |
| 6,926,004 B2 | 8/2005 | Schumacher |
| 7,069,932 B2 * | 7/2006 | Eaton et al. ............... 128/206.24 |
| 7,290,546 B2 * | 11/2007 | Sprinkle et al. ........... 128/206.24 |
| 2002/0011248 A1 * | 1/2002 | Hansen et al. ............ 128/207.11 |
| 2004/0025883 A1 | 2/2004 | Eaton et al. |
| 2004/0182398 A1 | 9/2004 | Sprinkle et al. |
| 2004/0216747 A1 | 11/2004 | Jones et al. |

FOREIGN PATENT DOCUMENTS

| | | |
|---|---|---|
| EP | 1334742 A2 | 8/2003 |
| JP | 11202796 | 7/1999 |
| WO | WO 00/78384 | 12/2000 |
| WO | WO0132250 A1 | 5/2001 |
| WO | WO03059427 A1 | 7/2003 |

* cited by examiner

PATIENT INTERFACE WITH FOREHEAD SUPPORT SYSTEM

CROSS-REFERENCE TO RELATED APPLICATIONS

This application is a Continuation (CON) under 35 U.S.C. §120 of U.S. patent application Ser. No. 10/654,379, filed Sep. 3, 2003, now U.S. Pat. No. 7,069,932, and also claims the benefit under the provisions of 35 U.S.C. §119(e) from provisional U.S. patent application Ser. No. 60/408,836 filed Sep. 6, 2002, the contents of each of which are incorporated herein by reference.

BACKGROUND OF THE INVENTION

1. Field of the Invention

The present invention pertains to a support system for a gas delivery mask, and, in particular to a forehead support system for a gas delivery mask and to a system for supplying a flow of gas to a patient that incorporates such a forehead support system.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure. Non-invasive ventilation and pressure support therapies involve the placement of a patient interface device, which is typically a nasal or nasal/oral mask, on the face of a patient to interface the ventilator or pressure support device with the airway of the patient so that a flow of breathing gas can be delivered from the pressure/flow generating device to the airway of the patient. It is known to maintain such masks on the face of a patient by a headgear having upper and lower straps, each having opposite ends threaded through connecting elements provided on the opposite sides and top of a mask.

Because such masks are typically worn for an extended period of time, it is important the headgear maintain the mask in a tight enough seal against a patient's face without discomfort. A problem arises in that in order for the mask to maintain a seal without any undue gas leaks around the periphery of the mask, the mask may be compressed against the patient's face.

It is known to provide forehead supports associated with gas delivery masks to provide a support mechanism between the mask and the patient's forehead. Gas delivery masks having forehead cushions, spacers or supports are described in U.S. Pat. Nos. 4,907,584; 5,243,971; 5,517,986; 5,570,689; 6,119,693 and 6,357,441. The forehead supports prevent the mask from exerting too much force on a patient's face at one general location by dispersing the load over a larger area, provides greater control of the force on the patient at certain pressure points, such as at the bridge of the nose, and provides stability to the mask.

Another mask with forehead support is disclosed in International Publication No. WO 00/78384 A1. In this arrangement a forehead support is adapted to be secured to a respiratory mask. The forehead support includes a joining member for securing to the mask and a cushion frame pivotally mounted to the joining member. While pivotal movement of the cushion frame to the joining member in one dimension allows the position of the forehead cushions to be adjusted, it does not optimize the ranges of positions for the forehead on a human head.

From the above-identified conventional masks, it can be appreciated that an advantage exists for increased stability of the gas delivery mask support. Another advantage exists for a forehead support that evenly distributes headgear strapping force. A further advantage exists for a mask that has an adjustable forehead support adaptable to a wide range of forehead configurations and sizes. Still yet, a further advantage exists for a forehead support bracket that allows the headgear and mask to be donned separately.

SUMMARY OF THE INVENTION

An exemplary embodiment of the present invention comprises a patient interface gas delivery mask having a forehead support including an adjustably mounted support arm and a forehead support bracket, and to a system for supplying a flow of gas to a patient that incorporates such a mask and forehead support.

An exemplary embodiment of the present invention provides a forehead support that includes a support arm adjustably mounted to the mask shell, thereby providing adjustment along an axis or curve which is normal to the plane of the mask shell to adjust for patients of different sizes and shapes. The adjustment assembly allows a patient to adjust the mask in such a way as to minimize leakage and pressure on certain areas of the face, such as the nose bridge.

An exemplary embodiment of the present invention includes a forehead support bracket which is slideably connected to the support arm. The forehead support bracket is self-aligning so that it allows the forehead pad to remain parallel to the patient's forehead at all times, thus enhancing comfort and stability. In an exemplary embodiment of the present invention, the forehead support bracket is removable from the support arm, allowing the headgear (with forehead support bracket attached) to be donned separately from the mask and support arm. This allows the patient to easily remove the mask without having to remove the headgear straps. An exemplary embodiment of the present invention further comprises a forehead support bracket having a forehead pad formed from the headgear itself.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", an and "the" include plural referents unless the context clearly dictates otherwise.

DETAILED DESCRIPTION OF THE EXEMPLARY EMBODIMENTS

In describing the presently preferred embodiments of the invention, the terms "horizontal" and "vertical" refer to the orientation of the mask as illustrated in the accompanying drawings.

Figure 1:
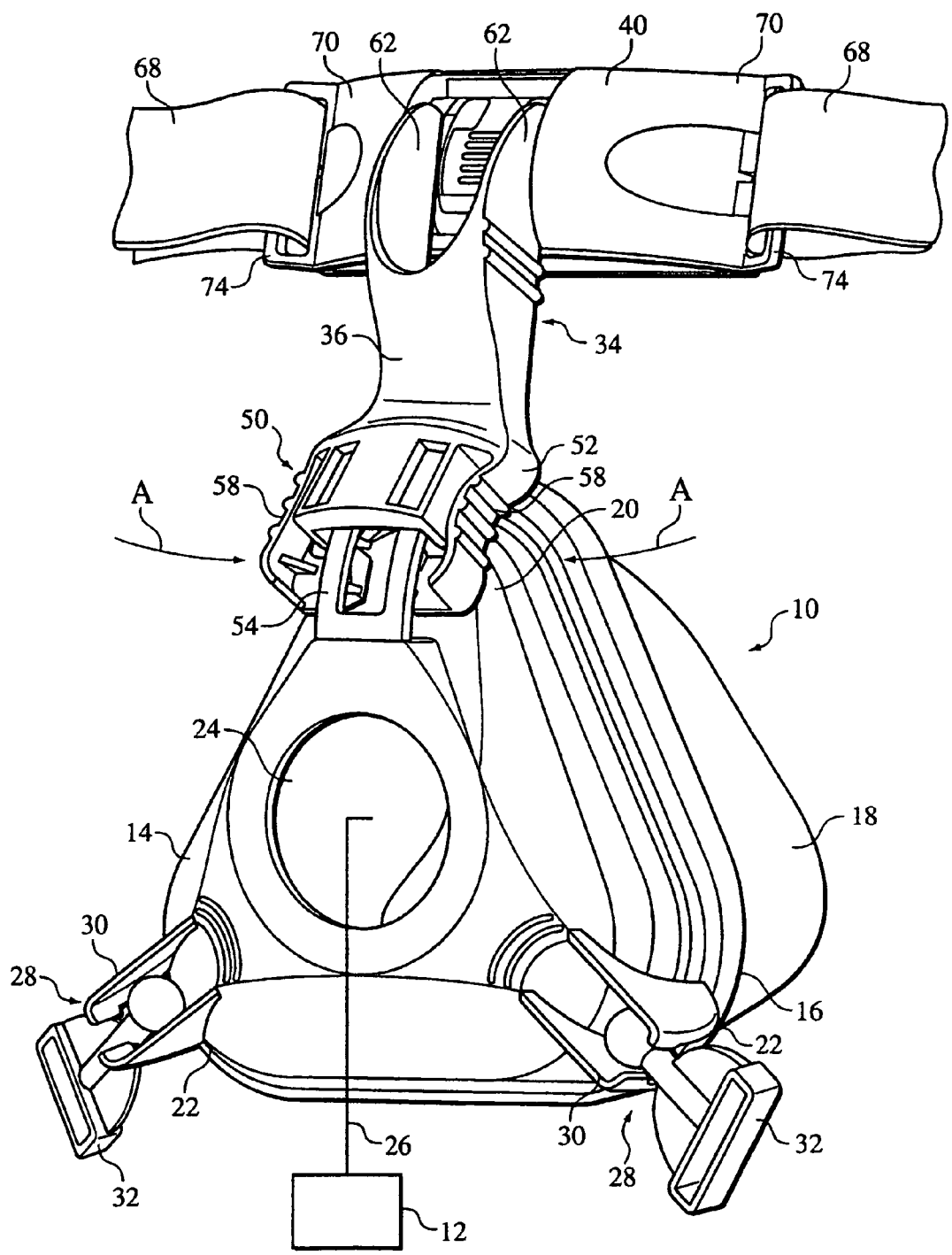
FIG. 1 is a perspective view of the mask and forehead support system according to the principles of an exemplary embodiment of the present invention shown (schematically) connected to a gas flow generating device.
Figure 2:
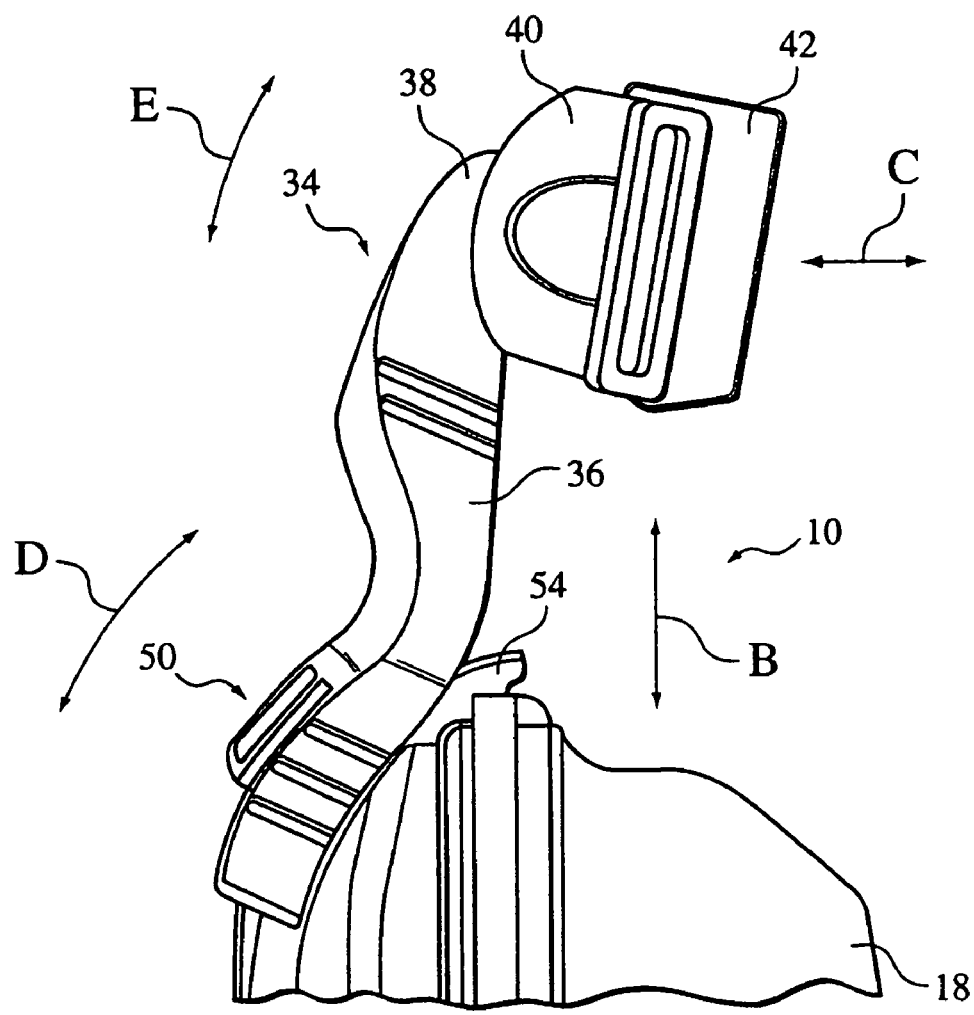
FIG. 2 is a partial side of the mask and forehead support system of FIG. 1.
Figure 3:
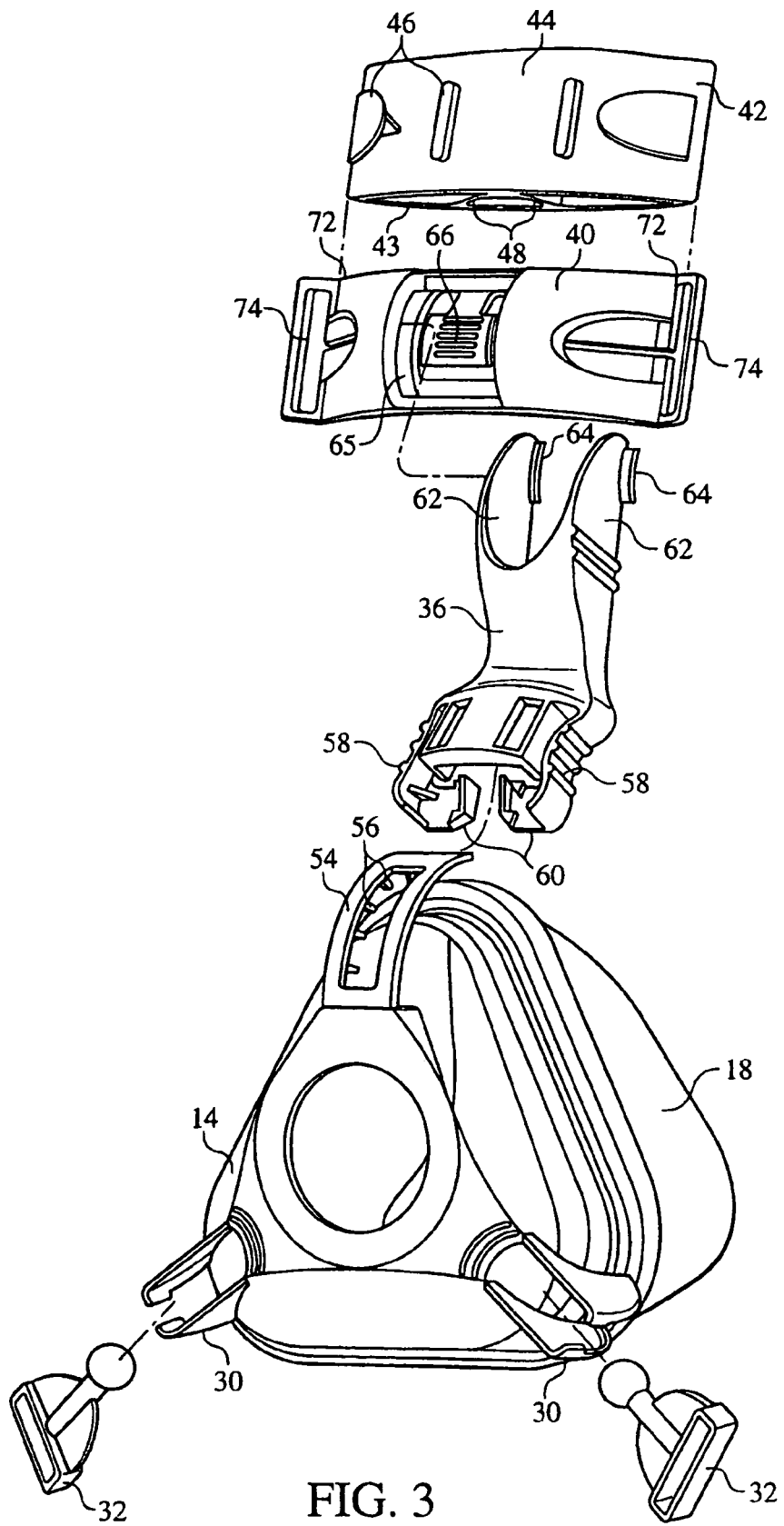
FIG. 3 is an exploded view of the mask and forehead support system of FIG. 1.

FIGS. 1-3 illustrate an exemplary embodiment of a gas delivery mask 10 according to the principles to the present invention. Gas delivery mask 10 functions as a patient interface device to communicate a flow of breathing gas between a patient's airway and a pressure generating device 12, such as a ventilator, CPAP device, autotitrating CPAP device, PPAP, PAV®, or variable pressure device, e.g. a BiPAP® device manufactured and distributed by Respironics, Inc. of Pittsburgh, Pa., in which the pressure provided to the patient varies with the patient's respiratory cycle so that a higher pressure is delivered during inspiration than during expiration.

Referring to FIGS. 1-3, there is illustrated a gas delivery mask 10 including a mask shell 14 or body portion which is preferably, but not necessarily, a generally rigid, formed structural shell having an open side that defines an annular portion 16 to which a resilient, relatively soft cushion or seal member 18 is attached. In the illustrated exemplary embodiment, mask shell 14 is substantially triangular in shape, having an upper apex angle 20 and two lower angles 22. Mask shell 14 includes an inlet opening 24 adapted to receive a gas supply conduit 26. Mask shell is preferably formed from rigid plastic, such as Polycarbonate. Seal member 18 is configured to receive a portion of the patient, such as the nose. Alternatively, mask 10 may, instead, comprise a nasal/oral mask configured to enclose the nose and mouth of a patient or an oral mask configured to enclose only the mouth of a patient.

In the illustrated exemplary embodiment, a lower headgear connector assembly 28 includes a pair of first connectors 30 rigidly attached to lower angles 22 of mask shell 14. Lower headgear straps in headgear assembly are selectively connected to mask 10 by means of a second connector 32. In the illustrated embodiment, a pair of second connectors 32, are removably connectable to end portions of headgear straps (not shown) and are also removably connectable to first connectors 30 on each side of mask shell 14. Alternately, lower headgear connector assembly 28 can be any suitable headgear connector assembly.

Likewise, the present invention contemplates the headgear can be any suitable headgear, i.e., and conventional headgear used in the patient interface field. For example, a typical headgear assembly comprises a headpiece (not shown) that overlies a portion of the patient's crania and with a pair of lower headgear straps and a pair of upper headgear straps extending therefrom to adjustably connect the headgear to the mask.

A forehead support 34, according to the illustrated exemplary embodiment, is provided at upper apex angle 20. Forehead support 34 in this embodiment is generally T-shaped and includes a support arm 36 which is connected at its upper end 38 to a horizontal forehead support bracket 40. Forehead support bracket 40 includes a forehead pad 42 on the patient contacting side.

Forehead pad 42 forms the actual contact point of forehead support bracket 40 to the forehead of the patient and is formed from an elastomeric cushioning material, such as silicon. In the illustrated embodiment, forehead pad 42 is rectangular in shape formed from a first wall 43 that contacts the patient and a second wall 44 having protrusions 46 that are connectable to respective openings (not illustrated) on forehead support bracket 40. A gap is provided between the first wall and the second wall so that the first wall moves toward the second wall when the mask is donned by a user and as the force on the forehead pad increases. A pair of retaining walls 48 extending between the first and second walls (43, 44) provide stability, for example, so that the first wall does not readily collapse onto the second wall as the force on forehead pad increases. The present invention contemplates that forehead pad 42 can be any suitable cushioning element and may include more than one pad and/or different sizes or variations or formed from alternative materials, such as gel, foam, or silicone.

The present invention further includes an adjustment assembly 50 in order to provide adjustment of the forehead support along an axis or curve, which is generally normal to the plane of mask shell 14. Adjustment assembly 50 allows the user to control the position of the forehead support, so that a common mask can be properly fitted to patients of different sizes and shapes. Moreover, adjustment assembly 50 allows a patient to adjust the mask in such a way as to minimize leakage and pressure on certain areas of the face, such as the nose bridge.

Adjustment assembly 50 is defined by components provided on mask shell 14 and a lower end 52 of support arm 36 so that support arm 36 is adjustably connectable to mask shell 14. More specifically, adjustment assembly 50 includes an arcuate attaching member 54 disposed on mask shell 14 and extending from a central portion of the mask shell above inlet opening 24 to a position spaced above upper apex angle 20 of mask shell 14. Attaching member 54 preferably is in the form of a track and includes multiple pairs of opposed teeth 56 (FIG. 3), where each tooth 56 extends in a horizontal direction. Adjustment assembly 50 also preferably includes two spaced apart flexible members 58 provided at the lower end of the support arm, where each flexible member 58 has a hook portion 60 at its distal end. It is to be understood, however, that a single row of teeth and a single flexible member corresponding therewith are also contemplated by the present invention.

When support arm 36 is connected to mask shell 14, attaching member 54 is received within support arm 36 with hook portions 60 of flexible members 58 engaging a pair of opposed teeth 56, thus locking support arm 36 into position relative to mask shell 14. Pressing flexible members 58 inwardly, as indicated by arrows A in FIG. 1, allows hook portions 60 to release from teeth 56 in order to change position to another set of opposed teeth 56 or in order to release support arm 36 and, thus, forehead support 34 from the mask shell entirely. Forehead support 34 is detachable from the mask shell 14 for cleaning or replacement. The present invention contemplates that any number of opposed teeth could be used. In addition, the teeth could be on the support arm and the hook portions could be on the attaching member.

It can appreciated from the above description and the accompanying illustrations, that the adjustment assembly of the present invention allows the forehead support, including the support arm, forehead support bracket and forehead pad, to move relative to the mask shell in two general directions simultaneously. First, the entire forehead support moves in a generally vertical direction, i.e., in a direction parallel to the plane in which the mask shell lies, as indicated by arrow B in FIG. 2, to move the forehead pad closer to or away from the mask shell. Second, the entire forehead support moves in a generally horizontal direction, i.e., in a direction generally perpendicular to the plane in which the mask shell lies, as indicated by arrow C in FIG. 2, to adjust the distance of the forehead support and the patient.

This simultaneous, two dimensional movement, which is indicated by arrow D in FIG. 2, is made possible by the curvilinear shape of the adjustment assembly, and, more particularly, the curvilinear shape of attaching member 54. This feature of the present invention allows the forehead support to be adjusted for the optimal, i.e., most comfortable, fit on the patient. In addition, the curvilinear movement of the forehead support allow the positioning of the forehead support to better approximate the shape of the human forehead than conventional forehead supports, which provide only pivoting movement about a fixed pivot point or linear movement along a single axis, e.g., along an axis correspond to arrow C in FIG. 2.

As best seen in FIG. 3, upper end 38 of support arm 36 is generally bifurcated forming two parallel vertical walls 62. A tongue 64 is perpendicularly and rigidly connected to the inside edge of each wall. Forehead support bracket 40 includes a pair of grooves 65 or tracks (one of which is shown in FIG. 3) extending in an arched shape and corresponding to tongues 64 for sliding receipt of the tongues. Movement of tongues 64 along grooves 65 causes the forehead support bracket 40 to move relative to the support arm 36 along a curvilinear or arc-shaped path, as indicated by arrow E in FIG. 2. It can be appreciated that the axis of rotation for the embodiment shown in FIGS. 1-3 is located at the centerpoint of the concentric circles that define arched grooves 65, which would be a virtual axis located a distance from the forehead support bracket. In this manner, the moveable attachment of the support art to the support bracket provides a connecting assembly that enhances automatic positioning of the forehead support on the patient.

Because this virtual centerpoint is actually located off of the support arm and the forehead support bracket, and, more particularly, below the surface of the patient's skin when wearing the mask, it provides self-alignment while creating a condition of high stability. The design of this virtual pivot is intended to reduce the likelihood of the forehead support bracket 40 tipping at an undesirable angle relative to the patient's skin when the mask is donned. In this way, the forehead support bracket 40 is self aligning to conform to the shape of the patient's head.

Forehead support bracket 40 is also detachable from support arm 36 by pressing a center tab 66 on forehead support bracket 40 and squeezing each of the two parallel vertical walls 62 on the upper end of the support arm. This allows detachment of the headgear for cleaning purposes or to allow a patient to don the headgear (with forehead support bracket 40 attached) and then attach support arm 36 to forehead support bracket 40. This also allows a patient to leave headgear straps 68 attached to the forehead support bracket at a desirable length when doffing and donning the mask so that the optimum headgear strap adjustment does not have to occur every time.

Each end portion 70 of the forehead support bracket, preferably includes a connector element 72 for securing an upper headgear strap 68. In this preferred embodiment, the connector element 72 is a female receiving slot for receiving a male quick release element 74 attached to an upper headgear strap 68. However, it should be apparent that other connection mechanisms could be used.

Alternative exemplary embodiments are illustrated in FIGS. 4-10. In these embodiments, many features are similar to those illustrated in FIGS. 1-3. Like reference numerals to those used in describing one embodiment will be used to denote like features in relation to other embodiments. It should be noted that the lower portion of the mask shell and lower headgear connector elements are not shown in these figures, because the relevant features can be garnered from reference to FIGS. 1 and 3.

Figure 4:
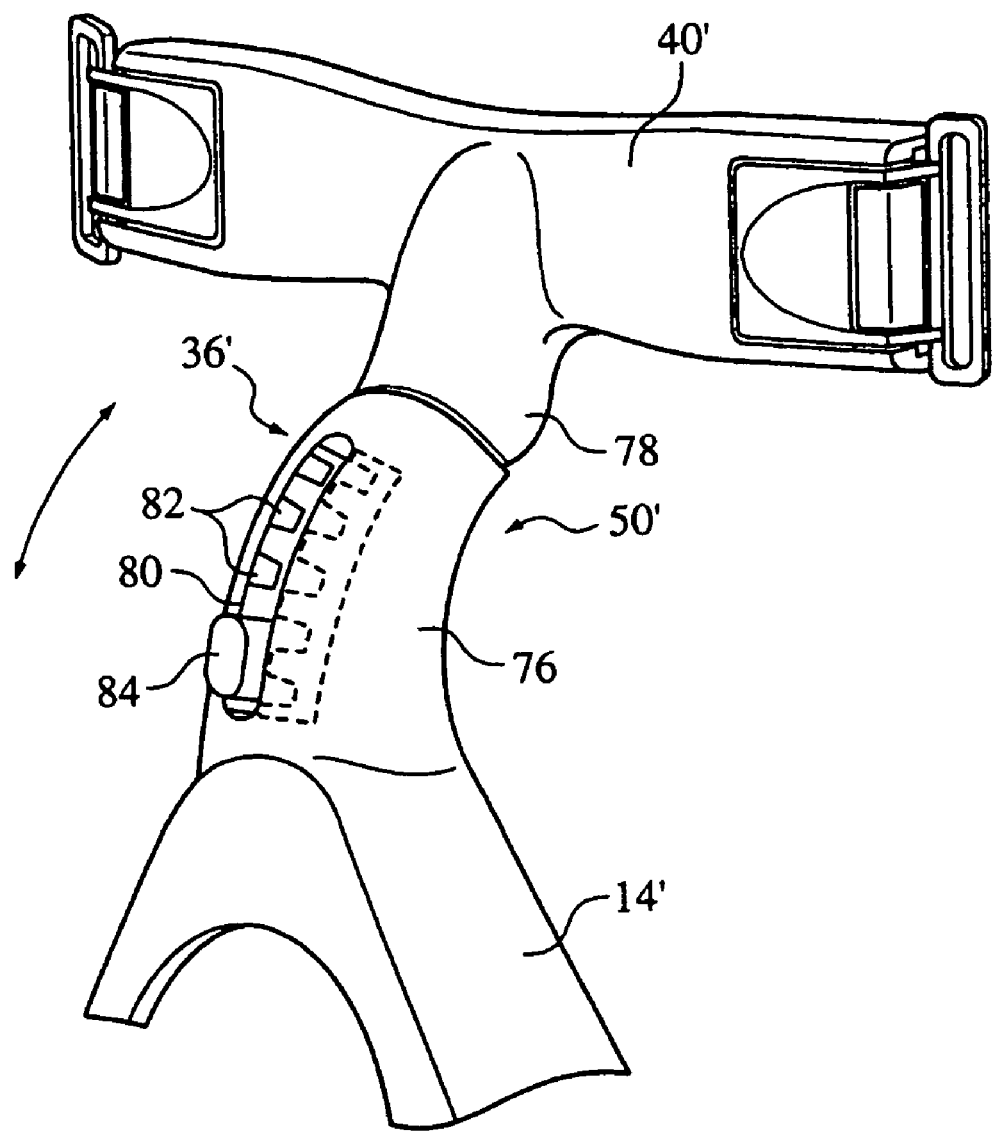
FIG. 4 is a partial perspective of a second embodiment of a mask and forehead support system according to the present invention.
Figure 5:
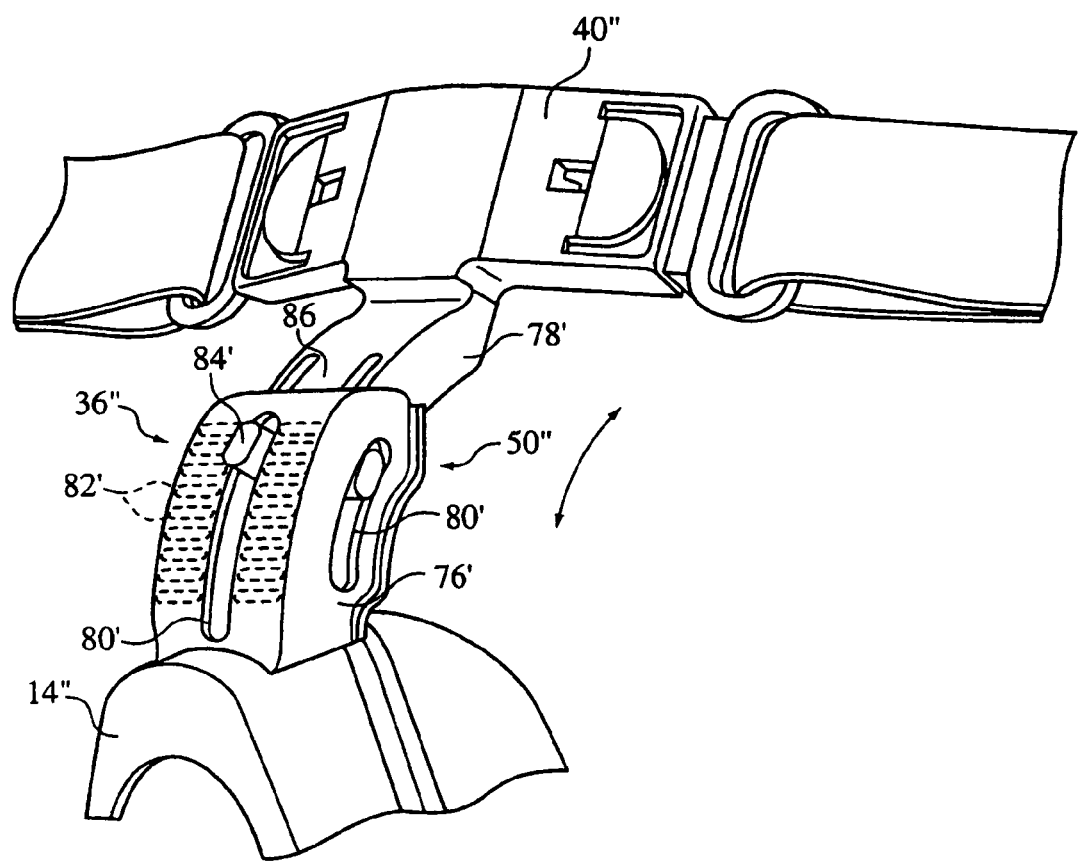
FIG. 5 is a partial perspective view of a third embodiment of a mask and forehead support system according to the present invention.
Figure 6:
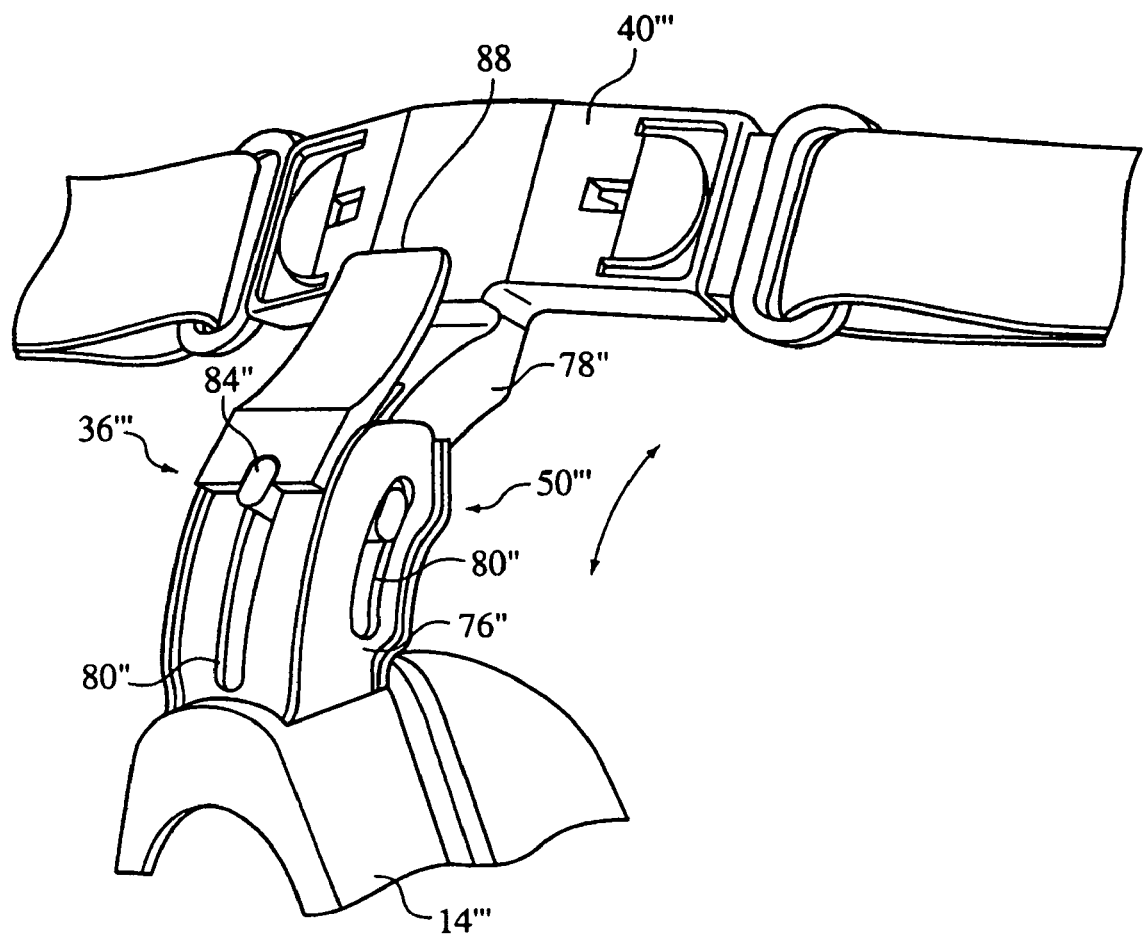
FIG. 6 is a partial perspective of a fourth embodiment of a mask and forehead support system according to the present invention.
Figure 7:
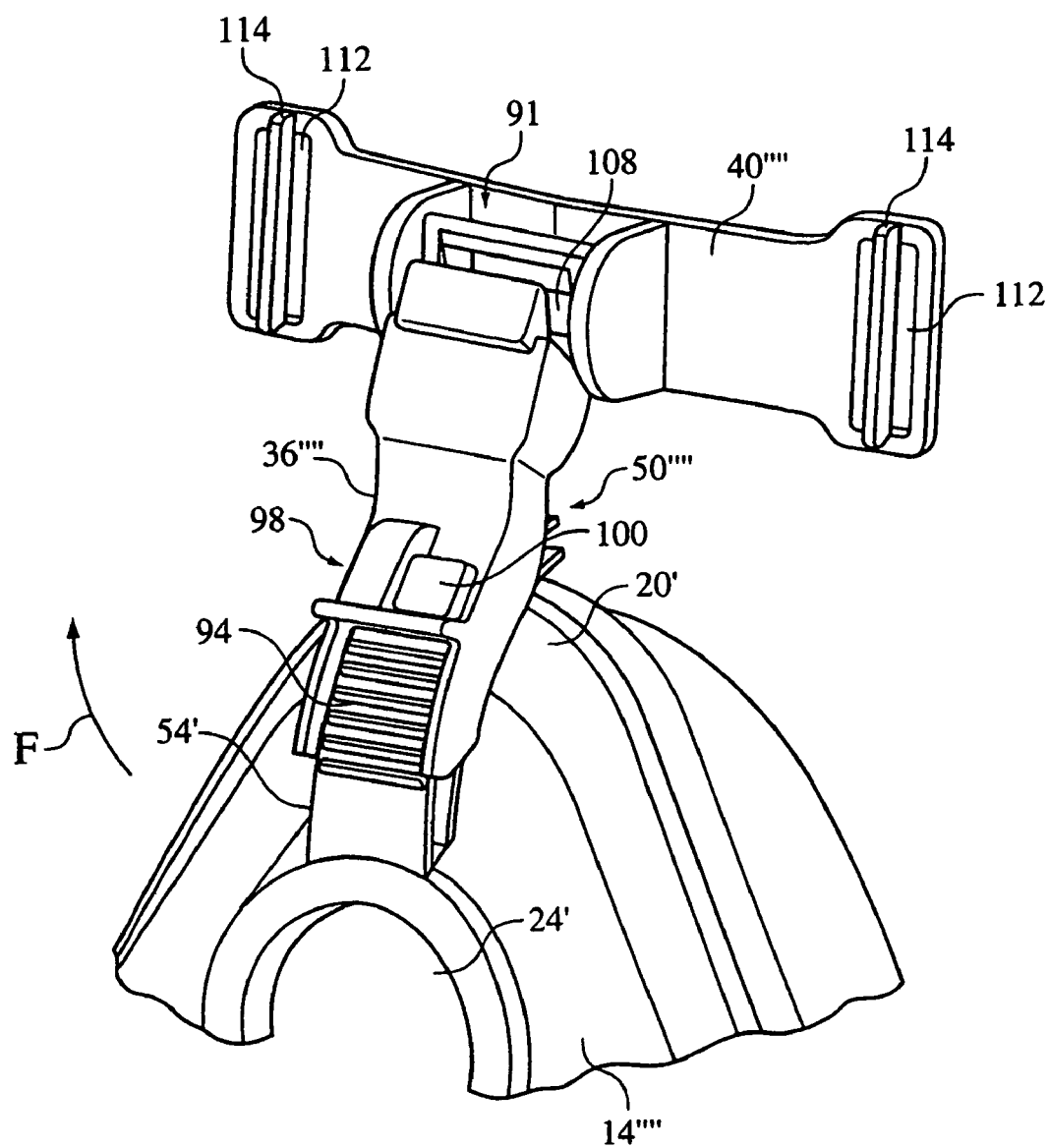
FIG. 7 is a partial perspective view of a fifth embodiment of a mask and forehead support system according to the present invention.
Figure 8:
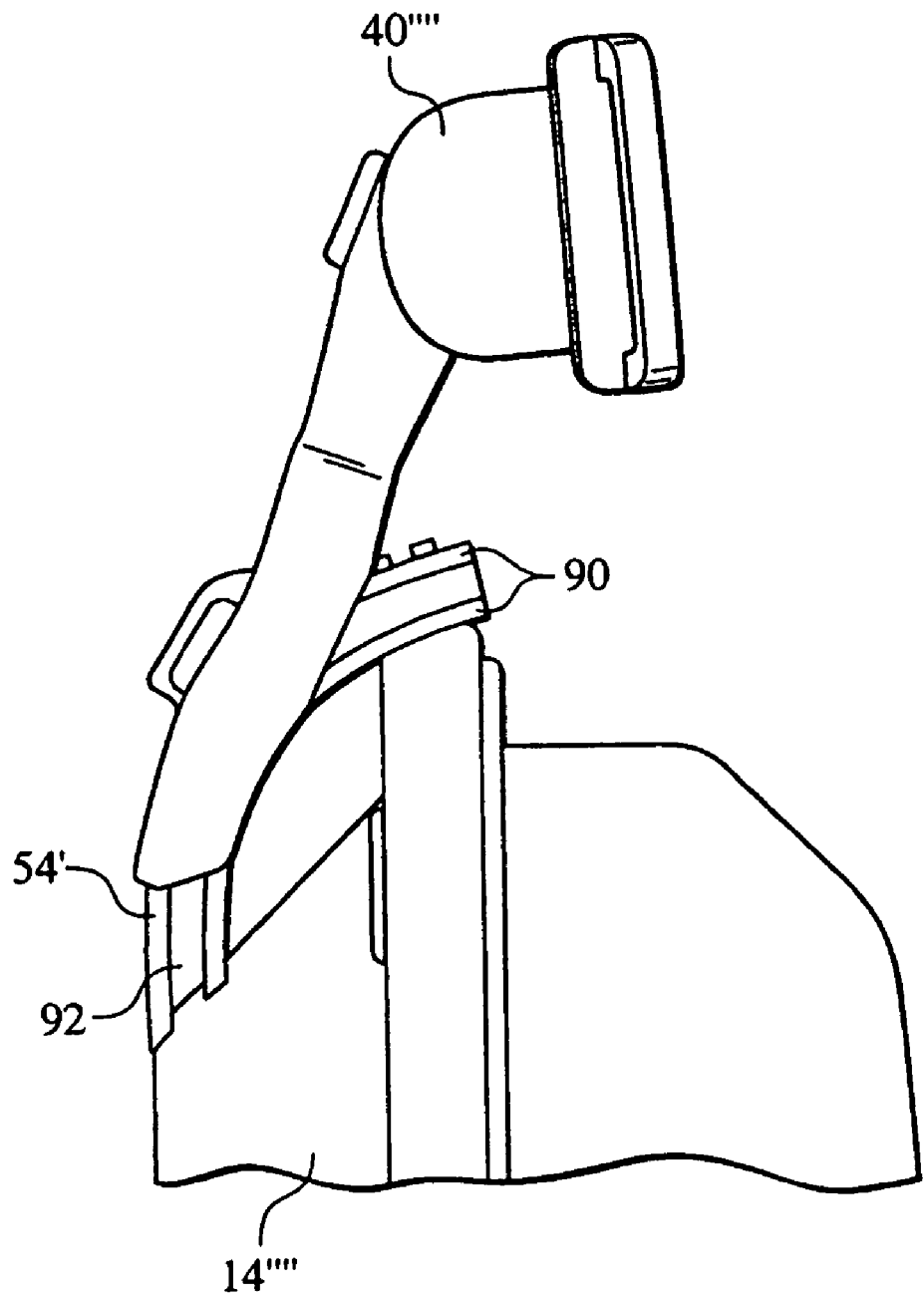
FIG. 8 is a partial side view of the mask and forehead support system of FIG. 7.

FIGS. 4-6 illustrate alternative embodiments for the adjustment assembly for the support arm of the forehead support. In a second embodiment illustrated in FIG. 4, adjustment assembly 50' of the present invention includes forming support arm 36' into two portions: a shell portion 76 connected to mask shell 14', and a bracket portion 78 connected to forehead support bracket 40'. The portions are connected to each other using a ratchet-type connection. Shell portion 76 has a generally tubular cross section having an exterior guide slot 80 having opposed ratchet-like teeth 82. The bracket portion 78 also has a generally tubular cross section adapted to slide within the shell portion 76 and having a central protrusion 84 corresponding to the guide slot 80. It is to be understood, however, that the present invention contemplates reversing the orientation of the tubular shell portion and the bracket portion, so that shell portion with the tubular slot is provided on the forehead support and the bracket portion that slides within a tubular slot is provided on the mask shell.

Like in the second embodiment of FIG. 4, the third embodiment illustrated in FIG. 5 includes an adjustment assembly 50" having a support arm 36" formed into two portions: a shell portion 76' connected to mask shell 14", and a bracket portion 78' connected to the forehead support bracket 40". In this embodiment, shell portion 76' and bracket portion 78' have generally U-shaped cross sections. The portions are connected to each other using a ratchet-type connection. Shell portion 76' has guide slots 80' on each side of its U-shape. Central guide slot 80' has opposed ratchet-like teeth 82'. Bracket portion 78' also is adapted to slide within shell portion 76' and has a central protrusion 84' corresponding to central guide slot 80' along with guide protrusions 84' corresponding to the other two guide slots 80' (only one of which is shown). In the embodiments of FIGS. 4 and 5, the central protrusions 84, 84' are located on a flexible member (86 shown in FIG. 5) having ratchet teeth (not illustrated) on either side of the central protrusion. When the central protrusion is pressed inwardly, flexible member 86 flexes inwardly allowing the ratchet teeth to disengage from each other, so that the shell portion and bracket portion can move relative to each other. As with the second embodiment, the relative male-female relationships between the bracket portion and the shell portion can be reversed.

Like in the third embodiment of FIG. 5, the fourth embodiment illustrated in FIG. 6 includes an adjustment assembly 50''' having a support arm 36''' formed into two portions: a shell portion 76'' having a U-shaped cross section connected to mask shell 14''', and a bracket portion 78'' having a U-shaped cross section connected to forehead support bracket 40'''. Shell portion 76'' also includes three guide slots 80'' (only two are shown) and the bridge portion 78'' includes corresponding protrusions 84''. However, rather than a system of ratchet teeth for adjustment, the shell portion also includes a pivoting member 88, pivotable about its lower end to provide a cam-locking action when locked in the position illustrated to supply a frictional force to effectively lock the relative position of the mask shell 14''' and forehead support bracket 40'''. This member 88 may be locked at any of an infinite number of positions within the range of motion, as opposed to other embodiments which have a set number of pre-determined positions.

In the fifth embodiment illustrated in FIGS. 7-12, the forehead support comprises a support arm 36'''' which is pivotally attached to a horizontal forehead support bracket 40'''' by means of a coupling system generally indicated at 91. Mask shell 14'''' further includes an adjustment assembly 50'''' adjustably connecting the support arm 36'''' to mask shell 14''''. Mask shell 14'''' includes an arcuate attaching member 54' rigidly attached to and extending from a central portion of mask shell 14'''' above inlet opening 24' to upper apex 20'. Attaching member 54' includes two concentrically arched ribs 90 forming a slot 92 therebetween. The outer curved portion includes a series of horizontal teeth and alternating grooves 94.

Support arm 36'''' includes a pair of arched engaging elements 96 (FIG. 9) that slide within the slot 92 on the attaching member 54'. A locking assembly 98 is provided to latch support arm 36'''' to attaching member 54'. In the illustrated embodiment, locking assembly 98 includes a latching slide pin 100, which is retained by support arm 36'''' and which slides in a direction perpendicular to the support arm. One or more teeth and grooves 102 (see FIG. 10) on the slide pin 100 are engageable with the teeth and grooves 94 on the attaching member 54'. Slide pin 100 of the illustrated embodiment is manually engaged but may also be spring-loaded.

Figure 9:
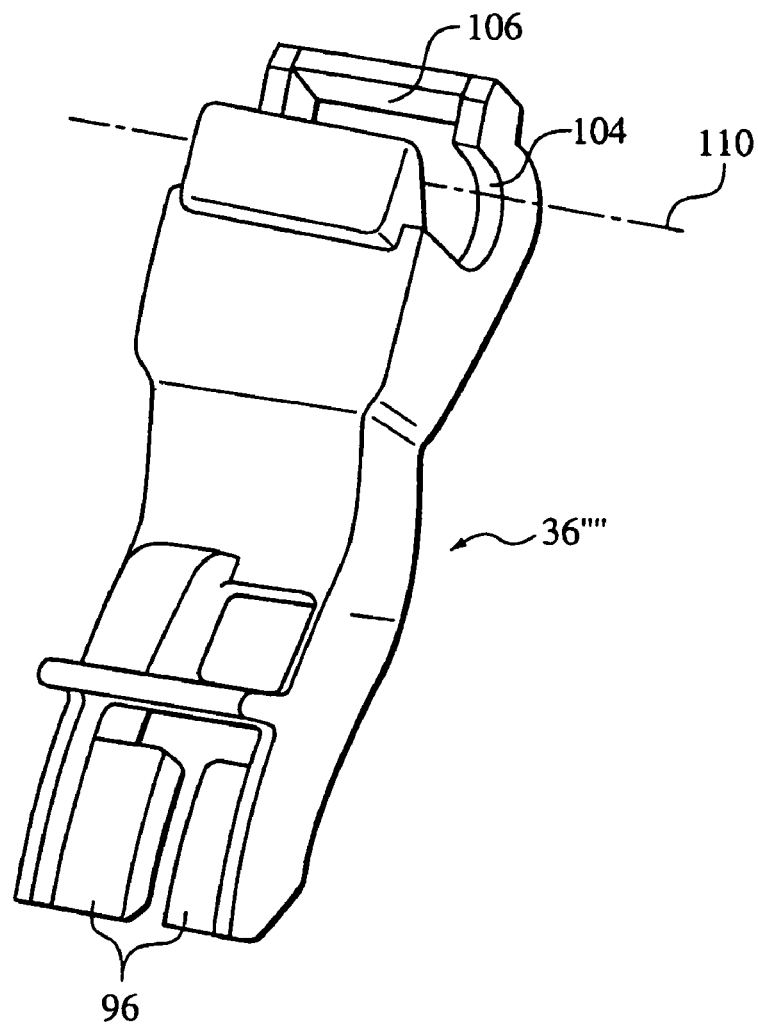
FIG. 9 is a perspective view of the support arm of FIG. 7.
Figure 10:
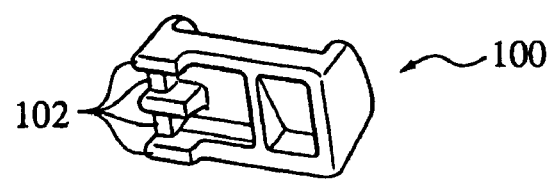
FIG. 10 is a bottom perspective view of the slide pin of FIG. 7.

As noted above, forehead support bracket 40'''' is pivotally connected to the upper end of support arm 36'''' via coupling system 91. In the illustrated embodiment, support arm 36'''' has a generally circular hole 104 formed through its upper end, with a slot 106 cut through a side at a predetermined angle, and forehead support bracket 40'''' has a horizontally oriented connecting bracket 108 that form the coupling system. Connecting bracket 108 has an oblong cross section. The long cross sectional dimension is approximately the same as the hole 104 diameter, and the short cross sectional dimensions approximately the same as the slot width. Connecting bracket 108 may be inserted into slot 106 in the support arm 36'''' when the two parts are at a certain angular position relative to one another. This position is out of the normal range of use. When forehead support bracket 40'''' is rotated into its normal range of use, it is locked in circular hole 104, but free to pivot within hole 104 about an axis of rotation 110 (FIG. 9).

Axis of rotation 110 for the embodiment shown in FIGS. 7-12 is along the center of the oblong cross-section on the connecting bracket 108. When support arm 36'''' and forehead support bracket 40'''' are attached, this coincides with the center of circular hole 104 in the upper end of support arm 36''''. This allows the patient to remove forehead support bracket 40'''' from support arm 36'''' and, thus, the mask, without having to remove the headgear straps from his or her head. Also, the forehead support bracket 40'''' is self aligning, so that it remains parallel to a patient's forehead regardless of forehead slope, mask position, or support arm 36'''' position.

Detachable forehead support bracket 40'''' in the embodiment of FIGS. 7-12, as well as the embodiment of FIGS. 1-3, allows a patient to don the headgear, with the forehead support bracket attached, separately from the mask. The mask is rotated to the proper angle for engagement/disengagement and attached to forehead support bracket 40''''. The lower headgear straps are then connected by the use of the disconnection device provided. To remove the mask, the patient disconnects the lower headgear straps, rotates the mask to the proper angle for engagement/disengagement as indicated by arrow in FIG. 7, and pulls the mask and support arm 36'''' away from forehead support bracket 40''''. This leaves the headgear, with forehead support bracket 40'''' attached to the headgear, on the patient's head. If the mask were to be replaced quickly, the patient could choose to leave the headgear and forehead support bracket 40'''' in place, as this would not be as obtrusive as wearing the complete mask assembly. This allows a patient to leave the bedside, get a drink, or other commonly performed activities without readjusting the headgear, and it would allow quick and easy replacement of the mask when desired.

Figure 11:
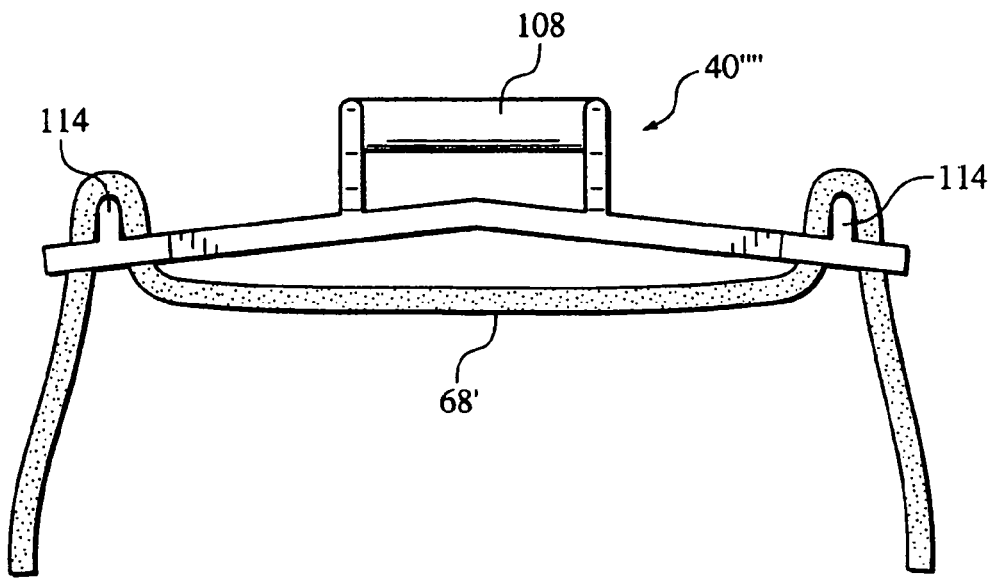
FIG. 11 is a top view of the forehead support bracket of FIG. 7 with the addition of a headgear strap.
Figure 12:
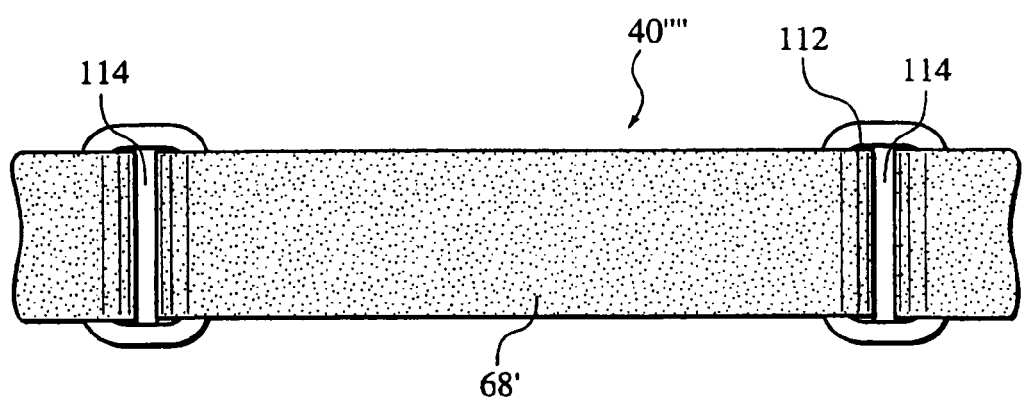
FIG. 12 is a back view of the forehead support bracket of FIG. 7 with the headgear strap.

As best seen in FIGS. 11 and 12, the present invention contemplates that headgear 68' itself can form the forehead pad. Headgear 68' passes through openings 112 having retaining rods 114 on each end of forehead support bracket 40''''. In this embodiment, headgear 68' is arranged across the forehead providing padding and evenly distributing the strapping force across the forehead.

The gas delivery mask of all of the embodiments functions as a patient interface device that communicates a flow of breathing gas between the patient's airway and pressure generating device, such as a ventilator, CPAP device (FIG. 1), or variable pressure device, e.g., a BiPAP® device manufactured and distributed by Respironics, Inc. of Pittsburgh, Pa., in which the pressure provided to the patient varies with the patient's respiratory cycle so that a higher pressure is delivered during inspiration than during expiration or an auto-titratition pressure support system where the pressure varies with the condition of the patient, such as whether the patient is snoring or experiencing an apnea or hypopnea.

Communicating a flow of breathing gas between the patient's airway and a pressure generating device includes delivering a flow of breathing gas to the patient from the pressure generating device and exhausting a flow of gas from the patient to ambient atmosphere. The system for delivering a breathing gas to a patient according to the present invention comprises a pressure or gas flow generating device 12 that produces a flow of gas; a conduit 26 having a first end portion operatively coupled to the gas flow generating device 12 and a second end portion, wherein the conduit 26 carries the flow of gas from the gas flow generating device 12 during operation of the system; a gas delivery mask assembly 10 coupled to the second end portion of the conduit; and a headgear.

In the illustrated embodiment, the adjustment assembly is configured to allow for curvilinear movement of the forehead support relative to the mask shell (see, e.g., arrow D in FIG. 2. It is to be understood, however, that the present invention contemplates that the adjustment assembly can provided other patterns of translational movement of the forehead support relative to the mask shell. For example, attaching member 54 can have an "S" shaped pattern, or a "J" shaped pattern so that the forehead support is moveable in an "S" or "J" pattern relative to the mask shell.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A gas delivery mask comprising:
   (a) a mask shell;
   (b) a curvilinear attachment member associated with the mask shell, the attachment member comprising a track having a track member and a plurality of teeth provided on the track member, each of the teeth extending outwardly from the track member in a respective first direction that is substantially normal to a surface of the track member; and
   (c) a forehead support comprising:
      (1) a support arm having a first portion and a second portion, wherein the first portion is coupled to the mask shell via the attachment member, and wherein the first portion is slideable along the attachment member in a curvilinear fashion wherein the first portion does not pivot or rotate about a fixed axis to permit movement of the entire forehead support in a first direction relative to the mask shell and a second direction relative to the mask shell simultaneously, wherein the first portion includes an attachment assembly having a flexible member structured to slideably receive the track member, and wherein the flexible member includes a hooked portion extending in a second direction, the second direction being transverse to the first direction associated with each of the teeth, the flexible member being structured to flex in the second direction to enable the hooked portion to selectively engage the teeth, wherein in order to release the hooked portion from engagement with any one of the teeth, the hooked portion must be flexed inwardly along the second direction toward a center of the attachment member, and
      (2) a forehead support bracket coupled to the second portion of the support arm.

2. The mask of claim 1, further comprising a connecting assembly movably coupling the forehead support bracket to the support arm.

3. The mask of claim 2, wherein the connecting assembly comprises a pivot connection between the forehead support bracket and the support arm that permits the support arm to rotate about a pivot axis relative to the forehead support bracket.

4. The mask of claim 2, wherein the second portion of the support arm comprises a first vertical wall and a second vertical wall parallel to the first vertical wall, the first vertical wall having a first arched tongue extending from an edge thereof and the second vertical wall having a second arched tongue extending from an edge thereof, the forehead support bracket having a first arched groove receiving the first arched tongue and a second arched groove receiving the second arched tongue, wherein movement of the first and second tongues along the first and second grooves, respectively, causes the forehead support bracket to move relative to the support arm in a curvilinear path.

5. The mask of claim 1, wherein the attachment member and the first portion of the support arm are configured to permit the support arm to move relative to the mask shell over a range of discrete positions.

6. The mask of claim 1, further comprising a cushion coupled to the mask shell.

7. The mask of claim 1, further comprising a headgear coupled to the forehead support, the mask shell, or both the forehead support and the mask shell.

8. A gas delivery mask comprising:
   a mask shell;
   a forehead support having a support arm having a first portion and a second portion and a forehead support bracket coupled to the second portion of the support arm; and
   an adjustment assembly coupling the first portion of the support arm to the mask shell such that the entire forehead support is moveable in a first direction relative to the mask shell and a second direction relative to the mask shell simultaneously, wherein the adjustment assembly includes a curvilinear attachment member associated with the mask shell, the attachment member comprising a track having a track member and a plurality of teeth provided on the track member, each of the teeth extending outwardly from the track member in a respective first direction that is substantially normal to a surface of the track member, wherein the first portion is slideable along the attachment member in a curvilinear fashion wherein the first portion does not pivot or rotate about a fixed axis to permit the movement in the first direction and the second direction during a single adjustment operation, wherein the first portion includes an attachment assembly including a flexible member structured to slideably receive the track member, and wherein the flexible member includes a hooked portion extending in a second direction, the second direction being transverse to the first direction associated with each of the teeth, the flexible member being structured to flex in the second direction to enable the hooked portion to selectively engage the teeth, wherein in order to release the hooked portion from engagement with any one of the teeth, the hooked portion must be flexed inwardly along the second direction toward a center of the attachment member.

9. The mask of claim 8, further comprising a connecting assembly movably coupling the forehead support bracket to the support arm.

10. The mask of claim 9, wherein the connecting assembly comprises a pivot connection between the forehead support bracket and the support arm that permits the support arm to rotate about a pivot axis relative to the forehead support bracket.

11. The mask of claim 9, wherein the second portion of the support arm comprises a first vertical wall and a second vertical wall parallel to the first vertical wall, the first vertical wall having a first arched tongue extending from an edge thereof and the second vertical wall having a second arched tongue extending from an edge thereof, the forehead support bracket having a first arched groove receiving the first arched tongue and a second arched groove receiving the second arched tongue, wherein movement of the first and second tongues along the first and second grooves, respectively, causes the forehead support bracket to move relative to the support arm in a curvilinear path.

12. The mask of claim 8, wherein the adjustment assembly and the first portion of the support arm are configured to permit the forehead support to move relative to the mask shell over a range of discrete positions.

13. A method of donning a gas delivery mask having a mask shell and support arm coupled thereto comprising:
(a) providing a mask comprising:
(1) a mask shell,
(2) a forehead support having a support arm having a first portion and a second portion and a forehead support bracket coupled to the second portion of the support arm, and
(3) an adjustment assembly coupling the first portion of the support arm to the mask shell, wherein the adjustment assembly includes a curvilinear attachment member associated with the mask shell, the attachment member comprising a track having a track member and a plurality of teeth provided on the track, each of the teeth extending outwardly from the track member in a respective first direction that is substantially normal to a surface of the track member, wherein the first portion is slideable along the attachment member in a curvilinear fashion wherein the first portion does not pivot or rotate about a fixed axis, wherein the first portion includes an attachment assembly including a flexible member structured to slideably receive the track member, and wherein the flexible member includes a hooked portion extending in a second direction, the second direction being transverse to the first direction associated with each of the teeth, the flexible member being structured to flex in the second direction to enable the hooked portion to selectively engage the teeth, wherein in order to release the hooked portion from engagement with any one of the teeth, the hooked portion must be flexed inwardly along the second direction toward a center of the attachment member, and wherein the performing step includes flexing the hooked portion inwardly along the second direction; and
(b) performing a single adjustment operation using the adjustment assembly causing the entire forehead support to move in a first direction relative to the mask shell and a second direction relative to the mask shell simultaneously during the single adjustment operation.

14. The method of claim 13, wherein donning the mask causes the forehead support bracket to self-adjust relative to the support arm.

15. The method of claim 13, wherein the forehead support is moveable relative to the mask shell over a range of discrete positions during the single adjustment operation.

16. A gas delivery mask comprising:
(a) a mask shell;
(b) a curvilinear attachment member associated with the mask shell, the attachment member comprising a track having a track member and a plurality of teeth provided on the track member; and
(c) a forehead support comprising:
(1) a support arm having a first portion and a second portion, wherein the first portion is coupled to the mask shell via the attachment member, and wherein the first portion is slideable along the attachment member in a curvilinear fashion wherein the first portion does not pivot or rotate about a fixed axis to permit movement of the entire forehead support in a first direction relative to the mask shell and a second direction relative to the mask shell simultaneously, wherein the first portion includes an attachment assembly having a flexible member structured to slideably receive the track member, and wherein the flexible member includes a hooked portion structured to selectively engage the teeth,
(2) a forehead support bracket coupled to the second portion of the support arm, and
(3) a connecting assembly movably coupling the forehead support bracket to the support arm, wherein the second portion of the support arm comprises a first vertical wall and a second vertical wall parallel to the first vertical wall, the first vertical wall having a first arched tongue extending from an edge thereof and the second vertical wall having a second arched tongue extending from an edge thereof, the forehead support bracket having a first arched groove receiving the first arched tongue and a second arched groove receiving the second arched tongue, wherein movement of the first and second tongues along the first and second grooves, respectively, causes the forehead support bracket to move relative to the support arm in a curvilinear path.

17. A gas delivery mask comprising:
a mask shell;
a forehead support having a support arm having a first portion and a second portion and a forehead support bracket coupled to the second portion of the support arm;
an adjustment assembly coupling the first portion of the support arm to the mask shell such that the entire forehead support is moveable in a first direction relative to the mask shell and a second direction relative to the mask shell simultaneously, wherein the adjustment assembly includes a curvilinear attachment member associated with the mask shell, the attachment member comprising a track having a track member and a plurality of teeth provided on the track member, wherein the first portion is slideable along the attachment member in a curvilinear fashion wherein the first portion does not pivot or rotate about a fixed axis to permit the movement in the first direction and the second direction during a single adjustment operation, wherein the first portion includes an attachment assembly including a flexible member structured to slideably receive the track member, and wherein the flexible member includes a hooked portion structured to engage the teeth; and
a connecting assembly movably coupling the forehead support bracket to the support arm, wherein the second portion of the support arm comprises a first vertical wall and a second vertical wall parallel to the first vertical wall, the first vertical wall having a first arched tongue extending from an edge thereof and the second vertical wall having a second arched tongue extending from an edge thereof, the forehead support bracket having a first arched groove receiving the first arched tongue and a second arched groove receiving the second arched tongue, wherein movement of the first and second tongues along the first and second grooves, respectively, causes the forehead support bracket to move relative to the support arm in a curvilinear path.

* * * * *